United States Patent
Gou et al.

(10) Patent No.: US 12,275,686 B2
(45) Date of Patent: Apr. 15, 2025

(54) NO DONOR COMPOUND, PREPARATION METHOD THEREOF, PHARMACEUTICAL COMPOSITION COMPRISING SAME, AND USE THEREOF

(71) Applicant: SOUTHEAST UNIVERSITY, Jiangsu (CN)

(72) Inventors: Shaohua Gou, Nanjing (CN); Wanxiang Yang, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 0 days.

(21) Appl. No.: 18/812,980

(22) Filed: Aug. 22, 2024

(65) Prior Publication Data

US 2024/0409500 A1  Dec. 12, 2024

Related U.S. Application Data

(63) Continuation of application No. PCT/CN2023/074113, filed on Feb. 1, 2023.

(30) Foreign Application Priority Data

Feb. 22, 2022 (CN) .................. 202210160994.8

(51) Int. Cl.
C07C 243/04 (2006.01)
A61K 31/196 (2006.01)
A61P 9/10 (2006.01)

(52) U.S. Cl.
CPC .......... *C07C 243/04* (2013.01); *A61K 31/196* (2013.01); *A61P 9/10* (2018.01)

(58) Field of Classification Search
CPC .... C07C 243/04; C07C 243/06; A61K 31/196
USPC ......................................................... 564/1
See application file for complete search history.

(56) References Cited

FOREIGN PATENT DOCUMENTS

| | | |
|---|---|---|
| CN | 1791403 A | 6/2006 |
| CN | 105832725 A | 8/2016 |
| WO | 2010035047 A1 | 4/2010 |

OTHER PUBLICATIONS

Wang, Peng George et al., Nitric Oxide Donors: Chemical Activities and Biological Applications, Chemical Reviews, 102(4): 1091-1134, 2002.
Hua, Wuyang et al., A Lysosome Specific Theranostic NO Donor Inhibits Cancer Cells by Stimuli Responsive Molecular Self-decompostion with An On-demand Fluorescence Pattern, Analyst, 144(22): 6681-6688, 2019.
International Search Report in PCT/CN2023/074113 mailed on Jun. 19, 2023, 6 pages.
Written Opinion in PCT/CN2023/074113 mailed on Jul. 10, 2023, 7 pages.

*Primary Examiner* — Ana Z Muresan
(74) *Attorney, Agent, or Firm* — Porus IP LLC (57) ABSTRACT

Disclosed is NO donor compound and preparation method, pharmaceutical composition, and use. The compound has a structure represented by formula The NO donor compound and the pharmaceutical composition thereof, as hypoxia-activated NO donors, may be prepared as drugs for treating myocardial hypoxic damage disease. The prepared drugs can exert efficacy at both the cellular level and the animal level, and the synthesis method of the compound is simple and easy to operate.

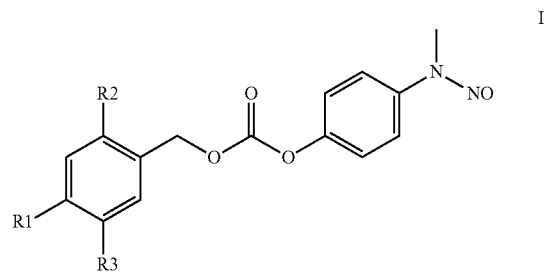

5 Claims, 4 Drawing Sheets

NO DONOR COMPOUND, PREPARATION METHOD THEREOF, PHARMACEUTICAL COMPOSITION COMPRISING SAME, AND USE THEREOF

CROSS-REFERENCE TO RELATED APPLICATIONS

This application is a Continuation of International Application No. PCT/CN2023/074113, filed on Feb. 1, 2023, which claims priority to Chinese Patent Application No. 202210160994.8, filed on Feb. 22, 2022, the entire contents of each of which are hereby incorporated by reference.

TECHNICAL FIELD

The present disclosure relates to NO donor compound and preparation method, pharmaceutical composition and use thereof, and in particular, to NO donor compound prepared as drug for treating myocardial hypoxic damage disease and preparation method, pharmaceutical composition, and application thereof.

BACKGROUND

Coronary heart disease is myocardial damage caused by myocardial tissue ischemia (cellular hypoxia) due to organic stenosis or obstruction of the coronary arteries, also known as ischemic heart disease. According to data report released by the Chinese Cardiovascular Disease Center in 2020, the number of people suffering from cardiovascular disease such as coronary heart disease in China has reached 290 million. At present, the high incidence and mortality of coronary heart disease pose a serious threat to people's health. Nitric oxide (NO) donor drugs are often used to treat coronary heart disease caused by ischemia because the NO donor drug is capable of releasing exogenous NO molecules in the body to promote vasodilation. However, existing drugs lack selectivity for hypoxia and cannot release sufficient NO in the hypoxic area, thus causing serious side effect.

In recent years, hypoxia-activated prodrugs have attracted extensive attention, which can promote selective release of active drug groups in hypoxic microenvironment, thereby reducing off target toxicity. Given that hypoxia is an important factor causing myocardial injury, applying this design concept to the structural design of NO donor drugs to obtain hypoxia-activated prodrugs is an effective method to improve the efficacy of such drugs and reduce side effect. Nitroreductase (NTR) exists in the heart, liver, kidney, lung, and brain tissues of mammals, which can catalyze the reduction of nitroaromatic compounds with hydrogen provided by NADPH and NADH under anaerobic condition. Therefore, nitroaromatic compounds are recognized as hypoxia-activated group, which may be used in the design of hypoxia-activated prodrugs. NTR in hypoxic cells can selectively reduce the nitro group on the aromatic ring, thereby promoting the release of active drug groups from prodrugs through intramolecular electron transfer. Since NTR is highly expressed in hypoxic cells, it can effectively promote the concentrated release of active drug groups from prodrugs in the hypoxic microenvironment, and thus, considering its hypoxia-activated properties, nitroaromatic compounds are combined with NO donors to obtain prodrugs that can release sufficient amounts of NO under hypoxia activation, which is of great significance for the treatment of cardiovascular diseases such as coronary heart disease.

SUMMARY

The purpose of the present disclosure: to solve the problems of poor efficacy and serious side effect of existing NO donor drugs in treating myocardial hypoxic damage disease, the present disclosure aims to provide NO donor compound that can effectively improve myocardial hypoxic damage in the hypoxic microenvironment, preparation method, pharmaceutical composition, and use thereof.

Technical solution: as the first aspect of the present disclosure, the NO donor compound has a structure of formula I:

wherein when R1 is nitro group, R2 is hydrogen, halogen, or C1-C4 alkyl, and R3 is hydrogen, halogen, or C1-C4 alkyl; or when R2 is nitro group, R1 is hydrogen, halogen, or C1-C4 alkyl, and R3 is hydrogen, halogen, or C1-C4 alkyl.

In some embodiments, the nitroaromatic compound, as hypoxia-activated group, is bonded with NO donor molecule through connecting group to obtain a hypoxia-activated NO donor compound.

In some embodiments, in the formula I, R1 is nitro group, R2 is hydrogen, halogen, or methyl, and R3 is hydrogen.

In some embodiments, the NO donor compound is selected from any of following compounds I1-I4:

As the second aspect of the present disclosure, the preparation method of the NO donor compound comprises obtaining NO donor compound I by acylation reaction between compound 1 and compound 2, including following steps.
- step (i): obtaining compound 1 by reacting 4-hydroxy (N-methyl) aniline hemisulfate with NaNO$_2$ in the presence of acetic acid; wherein the reaction temperature is 0° C., the solvent is acetic acid (AcOH), and the reaction time is 3 h.
- step (ii): obtaining compound 2 by reacting benzyl alcohol derivative with bis(trichloromethyl) carbonate (triphosgene, BTC) in the presence of N, N-diisopropylethylamine (DIPEA); wherein the reaction temperature is room temperature, the solvent is tetrahydrofuran (THF), and the reaction time is 5 h.
- step (iii): obtaining NO donor compound I by reacting Compound 1 with compound 2 in the presence of N, N-diisopropylethylamine; wherein the reaction temperature is room temperature, the solvent is dichloromethane (DCM), and the reaction time is 5 h.

The NO donor compound may be added to a pharmaceutically acceptable carrier to prepare common pharmaceutical preparations, such as tablets, capsules, syrups, suspensions, or injections. The preparations may be added with common pharmaceutical excipients such as spices, sweeteners, liquid/solid fillers, diluents, etc.

As the fourth aspect of the present disclosure, the NO donor compound and the pharmaceutical composition may be prepared as drugs for treating myocardial hypoxic damage disease. The NO donor compound is a hypoxia-activated NO donor compound, which is used to improve the viability of cardiomyocytes under the hypoxic condition, and specifically used to treat coronary heart disease. The NO donor compound may release NO in cells in the hypoxic microenvironment, effectively improving myocardial hypoxic damage.

Beneficial effects: compared with the prior art, the present disclosure has the following significant advantages.
(1) The NO donor compound and pharmaceutical composition can effectively release NO under the hypoxic condition, with the release amount of up to 40% or more, improve the vitality of cardiomyocytes, and serve as a hypoxia-activated NO donor both in vivo and in vitro.
(2) The NO donor compound and pharmaceutical composition have a wide range of use, which can be prepared as drug for treating myocardial hypoxic damage disease. The drug can exert their efficacy at both the R1, R2, and R3 are defined as above.

As the third aspect of the present disclosure, the pharmaceutical composition comprises the NO donor compound and a pharmaceutically acceptable carrier.

cellular level and the animal level and have a more excellent therapeutic effect.
(3) The preparation method of the NO donor compound is simple and easy to operate.

DETAILED DESCRIPTION

The present disclosure is further illustrated below in conjunction with examples.

Example 1: Preparation of N-methyl-N-nitroso-p-phenol (Compound 1)

4-Hydroxy (N-methyl) aniline hemisulfate (1.722 g, 10.0 mmol) was added to 50 mL of acetic acid under the dirk condition and dissolved to obtain a mix solution by ultrasound. Sodium nitrite solution, which was obtained by dissolving sodium nitrite (1.380 g, 20.0 mmol) in 10 ml of water, was added dropwise to the mixed solution in an ice-water bath for reaction, and the reaction was continued for 3 h in the ice-water bath after the addition was complete. After the reaction was completed, the reaction solution was transferred to a beaker, 50 mL of water was added into the beaker, the pH of the solution in the beaker was adjusted to 7 with saturated sodium bicarbonate solution, then the solution was extracted with ethyl acetate to obtain organic phases, and the organic phases were combined, dried with anhydrous sodium sulfate, and spin dried to obtain 1.46 g of the product with a yield of 96%.

$^1$H NMR (600 MHZ, DMSO-$d_6$): δ 9.79 (s, 1H), 7.41 (d, J=8.8 Hz, 2H), 6.89 (d, J=8.8 Hz, 2H), 3.38 (s, 3H) ppm.

Example 2: Preparation of p-nitrobenzyl chloroformate (Compound 2a)

P-nitrobenzyl alcohol (0.168 g, 1.1 mmol) and BTC (0.296 g, 1.0 mmol) were dissolved in 20 mL of anhydrous tetrahydrofuran to obtain a mixed solution, N, N-diisopropylethylamine (0.142 g, 1.1 mmol) was added into the mixed solution in the ice-water bath for reaction. The reaction was performed for 30 min under nitrogen protection, and then performed for 5 h at room temperature. After the reaction was completed, the reaction solution was concentrated, and a small amount of anhydrous tetrahydrofuran was used to remove excess phosgene in the reaction solution, and anhydrous dichloromethane was added into the concentrated solution to obtain anhydrous dichloromethane solution for using directly in the next step reaction.

Example 3: Preparation of 4-((methylnitroso) amino) phenyl (4-nitrobenzyl) carbonate (Compound I1)

Compound 1 (0.152 g, 1.0 mmol) and N, N-diisopropylethylamine (0.258 g, 2.0 mmol) were dissolved in 20 mL of anhydrous dichloromethane to obtain a mix solution, and the anhydrous dichloromethane solution containing compound 2a obtained in Example 2 was slowly dripped into the mixed solution in the ice-water bath for reaction. After the dripping was completed, the ice-water bath was removed and the reaction was performed for 5 h at room temperature. The reaction solution was washed 3 times with 0.5M dilute hydrochloric acid, water, and saturated saline solution, respectively, to separate the organic phase, the organic phase was dried overnight with anhydrous sodium sulfate, and then concentrated by rotary evaporation to obtain a yellow solid. The yellow solid was recrystallized with a mixed solvent of ethyl acetate and petroleum ether to obtain 285 mg of light-yellow crystal with a yield of 86%.

$^1$H NMR (600 MHz, DMSO-$d_6$): δ8.28-8.30 (m, 2H), 7.74-7.76 (m, 2H), 7.70-7.72 (m, 2H), 7.45-7.48 (m, 2H), 5.46 (s, 2H), 3.44 (s, 3H) ppm. $^{13}$C NMR (150 MHz, DMSO-$d_6$): δ153.15, 150.02, 147.87, 143.07, 140.37, 129.32, 124.15, 122.79, 121, 20, 69.03, 32.14 ppm. HRMS (m/z) (ESI): calcd for $C_{15}H_{14}N_3O_6[M+H]^+$: 332.08, found: 332.11.

Example 4: Preparation of 4-((methylnitroso) amino) phenyl (2-chloro-4-nitrobenzyl) carbonate (Compound I2)

Referring to the method described in Examples 2 and 3, using 2-chloro-4-nitrobenzyl alcohol as raw material, compound I2 was obtained as light-yellow crystal with a yield of 23%.

$^1$H NMR (600 MHZ, DMSO-d$_6$): δ8.38-8.39 (d, J=2.3 Hz, 1H), 8.28-8.30 (dd, 1H), 7.88-7.90 (d, J=8.5 Hz, 1H), 7.71-7.72 (m, 2H), 7.46-7.48 (m, 2H), 5.49 (s, 2H), 3.44 (s, 3H) ppm. $^{13}$C NMR (150 MHz, DMSO-d$_6$): δ 152.99, 149.95, 148.49, 140.41, 140.18, 133.62, 131.17, 124.78, 122.96, 122.77, 121.25, 66.92, 32.20 ppm. HRMS (m/z) (ESI): calcd for C$_{15}$H$_{13}$ClN$_3$O$_6$Na [M+Na]$^+$: 388.03, found: 388.10.

Example 5: Preparation of 4-((methylnitroso) amino) phenyl (2-methyl-4-nitrobenzyl) carbonate (Compound I3)

Referring to the method described in Examples 2 and 3, using 2-methyl-4-nitrobenzyl alcohol as raw material, compound I3 was obtained as light-yellow crystal with a yield of 45%.

$^1$H NMR (600 MHZ, DMSO-d$_6$): δ8.15-8.16 (d, J=2.2 Hz, 1H), 8.10-8.14 (dd, J=8.4, 2.4 Hz, 1H), 7.71-7.73 (d, J=2.2 Hz, 1H), 7.68-7.70 (m, 2H), 7.45-7.48 (m, 2H), 5.44 (s, 2H), 3.44 (s, 3H), 2.47 (s, 3H) ppm. $^{13}$C NMR (150 MHz, DMSO-d$_6$): δ153.11, 150.01, 147.78, 141.17, 140.37, 139.16, 129.71, 125.06, 122.80, 121.49, 121.21, 67.66, 32.17, 18.77 ppm. HRMS (m/z) (ESI): calcd for C$_{16}$H$_{15}$N$_3$O$_6$[M+H]$^+$: 346.10, found: 346.10.

Example 6: Preparation of 4-((methylnitroso) amino) phenyl (2-nitrobenzyl) carbonate (Compound I4)

Referring to the method described in Examples 2 and 3, 2-nitrobenzyl alcohol was used as a raw material, compound I4 was obtained as light-yellow crystal with a yield of 73%.

$^1$H NMR (600 MHZ, DMSO-d$_6$): δ8.17-8.19 (dd, 1H), 7.85-7.88 (m, 1H), 7.79-7.80 (m, 1H), 7.70-7.73 (m, 2H), 7.68-7.69 (m, 1H), 7.45-7.47 (m, 2H), 5.65 (s, 2H), 3.44 (s, 3H) ppm. $^{13}$C NMR (150 MHz, DMSO-d$_6$): δ153.04, 149.98, 147.82, 140.40, 134.85, 130.81, 130.25, 130.06, 125.49, 122.77, 121.24, 67.09, 32.16 ppm. HRMS (m/z) (ESI): calcd for C$_{15}$H$_{14}$N$_3$O$_6$[M+H]$^+$: 332.09, found: 332.02.

Example 7: Preparation of 4-((methylnitroso) amino) phenyl (2-nitro-4-chlorobenzyl) carbonate (Compound I5)

Referring to the method described in Examples 2 and 3, using 2-nitro-4-chlorobenzyl alcohol as raw material, compound I5 was obtained as light-yellow crystal with a yield of 46%.

$^1$H NMR (600 MHZ, DMSO-d$_6$): δ8.26-8.27 (d, J=2.2 Hz, 1H), 7.94-7.96 (dd, 1H), 7.81-7.83 (d, J=8.4 Hz, 1H), 7.70-7.72 (m, 2H), 7.45-7.46 (m, 2H), 5.62 (s, 2H), 3.44 (s, 3H) ppm. $^{13}$C NMR (150 MHz, DMSO-d$_6$): δ152.94, 149.96, 148.47, 140.42, 134.51, 134.21, 131.84, 129.81, 125.32, 122.75, 121.24, 66.53, 32.15 ppm. HRMS (m/z) (ESI): calcd for C$_{15}$H$_{13}$ClN$_3$O$_6$Na [M+Na]$^+$: 388.03, found: 388.00.

Example 8: Preparation of 4-((methylnitroso) amino) phenyl (2-nitro-4-bromobenzyl) carbonate (Compound I6)

Referring to the method described in Examples 2 and 3, using 2-nitro-4-bromobenzyl alcohol as raw material, compound I6 was obtained as light-yellow crystal with a yield of 33%.

$^1$H NMR (600 MHZ, DMSO-d$_6$): δ8.36-8.37 (d, J=2.1 Hz, 1H), 8.07-8.09 (dd, 1H), 7.73-7.75 (d, J=8.3 Hz, 1H), 7.70-7.72 (m, 2H), 7.44-7.46 (m, 2H), 5.60 (s, 2H), 3.44 (s, 3H) ppm. $^{13}$C NMR (150 MHz, DMSO-d 6): δ152.94, 149.96, 148.49, 140.42, 137.45, 131.94, 130.19, 128.03, 122.75, 122.16, 121.24, 66.58, 32.15 ppm. HRMS (m/z) (ESI): calcd for C$_{15}$H$_{13}$BrN$_3$O$_6$[M+H]$^+$: 431.98, found: 431.90.

Example 9: Preparation of 4-((methylnitroso) amino) phenyl (2-nitro-4-methylbenzyl) carbonate (Compound 17)

Referring to the method described in Examples 2 and 3, using 2-nitro-4-methylbenzyl alcohol as raw material, compound I7 was obtained as light-yellow crystal with a yield of 51%.

$^1$H NMR (600 MHz, DMSO-$d_6$): δ8.00-8.01 (m, 1H), 7.70-7.72 (m, 2H), 7.66-7.67 (d, J=0.9 Hz, 2H), 7.43-7.46 (m, 2H), 5.60 (s, 2H), 3.44 (s, 3H), 2.44 (s, 3H) ppm. $^{13}$C NMR (150 MHz, DMSO-$d_6$): δ153.04, 149.99, 147.77, 140.57, 140.38, 135.29, 130.22, 127.75, 125.56, 122.74, 121.20, 67.02, 32.12, 20.74 ppm. HRMS (m/z) (ESI): calcd for $C_{16}H_{16}N_3O_6$[M+H]$^+$: 346.10, found: 345.90.

Example 10: Preparation of 4-((methylnitroso) amino) phenyl (2-nitro-5-chlorobenzyl) carbonate (Compound 18)

Referring to the method described in Examples 2 and 3, using 2-nitro-5-chlorobenzyl alcohol as raw material, compound I8 was obtained as light-yellow crystal with a yield of 37%.

$^1$H NMR (600 MHz, DMSO-$d_6$): δ8.21-8.23 (d, J=8.8 Hz, 1H), 7.83-7.84 (d, J=2.3 Hz, 1H), 7.76-7.79 (dd, 1H), 7.71-7.73 (m, 2H), 7.46-7.48 (m, 2H), 5.65 (s, 2H), 3.44 (s, 3H) ppm. $^{13}$C NMR (150 MHz, DMSO-$d_6$): δ152.82, 149.98, 146.36, 140.43, 139.48, 133.27, 130.05, 129.67, 127.63, 122.76, 121.23, 66.56, 32.14 ppm. HRMS (m/z) (ESI): calcd for $C_{15}H_{13}ClN_3O_6Na$ [M+Na]$^+$: 388.03, found: 388.00.

Example 11: Preparation of 4-((methylnitroso) amino) phenyl (2-nitro-5-methylbenzyl) carbonate (Compound 19)

Referring to the method described in Examples 2 and 3, using 2-nitro-5-methylbenzyl alcohol as raw material, compound I9 was obtained as light-yellow crystal with a yield of 48%.

$^1$H NMR (600 MHz, DMSO-$d_6$): δ8.09-8.11 (d, J=8.4 Hz, 1H), 7.72-7.73 (d, J=2.2 Hz, 1H), 7.71-7.72 (d, J=2.3 Hz, 1H), 7.57-7.58 (m, 1H), 7.48-7.49 (m, 1H), 7.46-7.47 (d, J=2.3 Hz, 1H), 7.45-7.46 (d, J=2.2 Hz, 1H), 5.63 (s, 2H), 3.44 (s, 3H), 2.47 (s, 3H) ppm. $^{13}$C NMR (150 MHz, DMSO-$d_6$): δ153.00, 150.01, 145.93, 145.49, 140.40, 130.95, 130.47, 130.26, 125.70, 122.78, 121.24, 67.21, 32.15, 21.53 ppm. HRMS (m/z) (ESI): calcd for $C_{16}H_{15}N_3O_6Na$ [M+Na]$^+$: 368.09, found: 368.10.

Example 12: Detection of NO Release Level of the Compound after Interacting with H9c2 Cells Under Normoxia or Hypoxia Condition Using Griess Method H9c2 cells were revived, cultured with DMEM medium, and placed in a carbon dioxide incubator to allow the cells to adhere to the wall for growth. After the cells grew to reach an appropriate density, cells were inoculated in a multi-well plate and placed in the carbon dioxide incubator for culture for 24 h at 37° C., 5% $CO_2$, and saturated humidity until the cells adhered to the wall, the supernatant was discarded, and 2 mL of fresh DMEM medium was added. Then, a certain concentration (5, 10, 15 μM) of compounds and the reference drug of isosorbide dinitrate were added. After culturing in a normoxic incubator (37° C., 21% $O_2$) or an anoxic incubator (37° C., 1% $O_2$) for 4 h, the supernatant was removed, and the cells in the multi-well plate were collected in 1.5 mL centrifuge tubes and centrifuged at 1000 rpm for 5 min, the supernatant was discarded, 1 mL of PBS was added into the centrifuge tubes to resuspend the cells, and the cells were centrifuged again, the PBS was discarded. 100 μL of cell lysis buffer (special for NO measurement) was added to the centrifuge tubes, placed on ice for half a minute, and then centrifuged for 5 min at 4° C. and 13300 rpm, and the supernatant was collected. 50 μL of the supernatant was taken in a 96-well plate, three parallel groups were set for each sample, and 50 μL of Griess reagent I and 50 μL of Griess reagent II were added in sequence. The OD value of each well was measured at 540 nm with a full-wavelength microplate reader, and the NO concentration was calculated using the standard curve, as shown in Tables 1 and 2.

TABLE 1

NO release amount of H9c2 cells treated with compounds
for 4 h under the normoxia condition

| Compound | Concentration (μM) NO release amount (%) * | | |
|---|---|---|---|
| | 5 | 10 | 15 |
| I1 | 0.24 | 0.84 | 0.16 |
| I2 | 1.58 | 3.34 | 0.93 |
| I3 | 0.43 | 0.92 | 0.32 |
| I4 | 1.02 | 2.35 | 0.98 |
| I5 | —[a] | 0.15 | — |
| I6 | — | 0.17 | — |
| I7 | — | 0.12 | — |
| I8 | — | 0.27 | — |
| I9 | — | 0.23 | — |
| Isosorbide dinitrate[b] | 36.30 | 41.63 | 36.89 |

* denotes that NO release amount = measured NO concentration/calculated NO concentration, data are expressed as the mean SD of three independent experiments: *p < 0.05, **p < 0.01;
[a] denotes that the NO release amount is not measured, and
[b] denotes calculation based on ½ of the NO release amount.

TABLE 2

NO release amount of H9c2 cells treated with
compounds for 4 h under the hypoxia condition

| Compound | Concentration (μM) NO release (%) * | | |
|---|---|---|---|
| | 5 | 10 | 15 |
| I1 | 25.24 | 24.38 | 20.15 |
| I2 | 34.75 | 30.96 | 27.37 |
| I3 | 40.58 | 45.42 | 43.21 |
| I4 | 20.78 | 20.62 | 18.33 |
| I5 | —[a] | 0.96 | — |
| I6 | — | 0.94 | — |
| I7 | — | 1.83 | — |
| I8 | — | 0.93 | — |
| I9 | — | 0.95 | — |
| Isosorbide dinitrate[b] | 22.73 | 27.41 | 24.90 |

* denotes that NO release amount = measured NO concentration/calculated NO concentration, data are expressed as the mean SD of three independent experiments: *p < 0.05, **p < 0.01;
[a] denotes that the NO release amount is not measured,
[b] denotes calculation based on ½ of the NO release amount.

As shown in Tables 1 and 2, the NO release amount of cells after being treated with different concentrations of compounds under the normoxia condition are very small, which are all lower than the maximum release amount of compound I2 (<3.34%, 10 μM). But under the hypoxia condition, except for compounds I5-I9, after the cells being treated with different concentrations of compounds I1-I4, the compounds I1-I4 can effectively cause release of NO in the cells, with the NO release amount ranging from 20.15% to 45.45%, indicating hypoxia-activated NO donors. The reference drug of isosorbide dinitrate (ISDN) releases a certain amount of NO in the cells after treating cells under the normoxia or hypoxia condition. The isosorbide dinitrate causes a large NO release amount (up to 41.63%, (10 μM)) in the cells under the normoxia condition. The isosorbide dinitrate also cause a NO release amount in the cells under the hypoxia condition, but the NO release amount is less than that under the normoxia condition, and lower than the NO release amount of compounds I2 and I3 under the hypoxia condition.

Example 13: Improvement Effect of the Compound on the Vitality of H9c2 Cells Under the Normoxia or Hypoxia Condition The cells were washed twice with 5 mL PBS, 1 mL trypsin was added to digest the monolayer cultured H9c2 cells, a single cell suspension was prepared with serum-containing culture medium, and 5000-10000 cells per well were inoculated in a 96-well culture plate. The volume of culture medium per well is 100 μL, and the edge wells are filled with sterilized pure water. The culture plate was moved into a carbon dioxide incubator for culture for 24 h at 37° C., 5% $CO_2$, and saturated humidity until the cells adhere to the wall. 100 μL culture medium in the well was aspirated, 50 μL fresh culture medium was added into the well, and different concentrations of compounds and reference drug isosorbide dinitrate were given respectively to the well. 50 μL drug was added to each well, 3 parallel groups and 1 normoxic group without drug addition as control were set, and concentration gradient of the drug is 10, 1, 0.1, 0.01, 0.001 μM. The normoxic group was incubated in a normal incubator at 5% $CO_2$ and 37° C. for 4 h; and the hypoxic group was incubated in a hypoxic incubator (concentration of $O_2 \leq 1\%$) at 37° C. for 4 h. After the culture was completed, 10 μL CCK8 reagent was added to each well and the normoxic group and the hypoxic group continued to be cultured in a normoxic incubator for 4 h, and the culture was terminated. The absorbance of each well was measured at 450 nm with a microplate reader to calculate the cell survival rate of cells at different concentrations, as shown in FIGS. 1A and 1B.

Figure 1A:
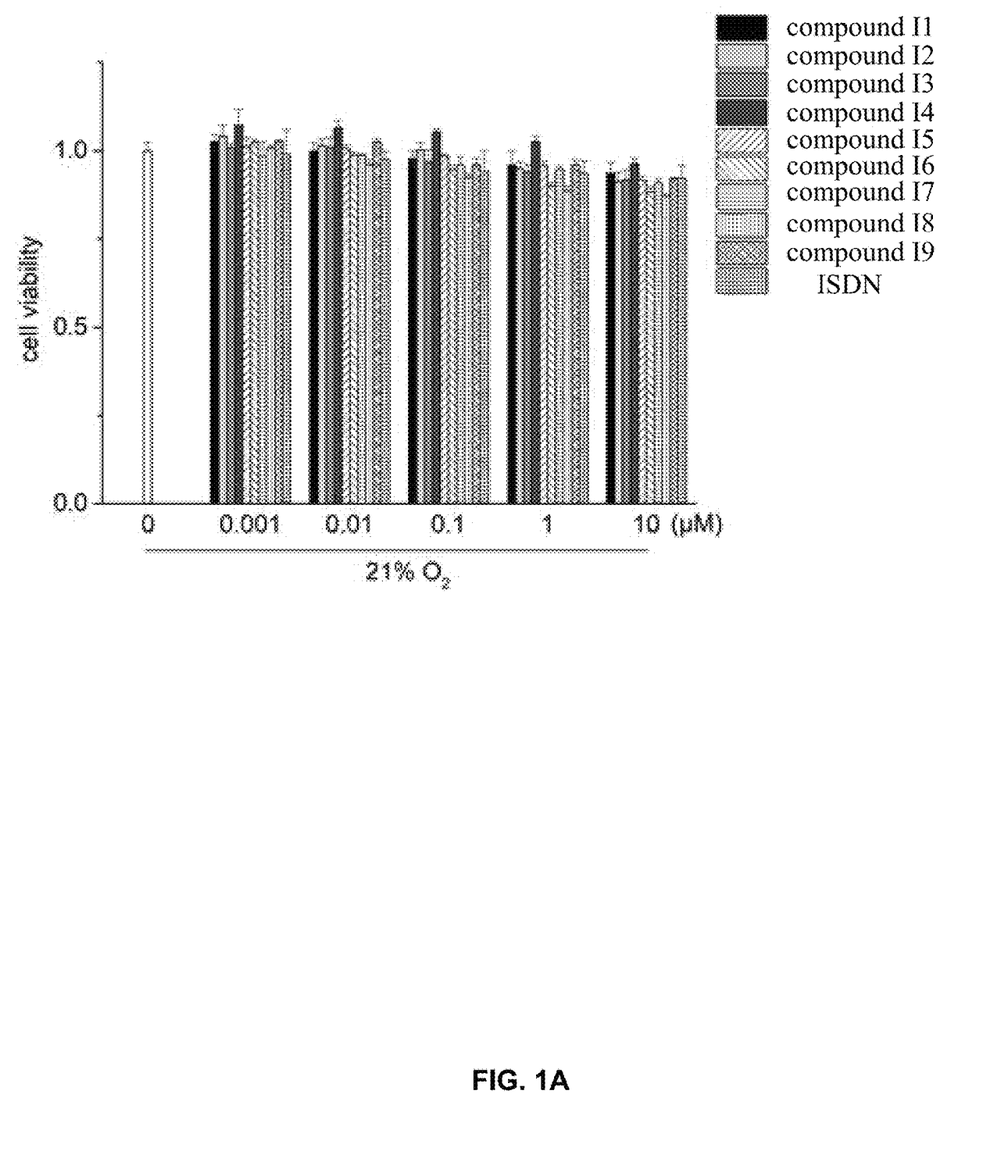
FIG. 1A shows the effect of the NO donor compound on improving the vitality of H9c2 cells under the normoxic condition.
Figure 1B:
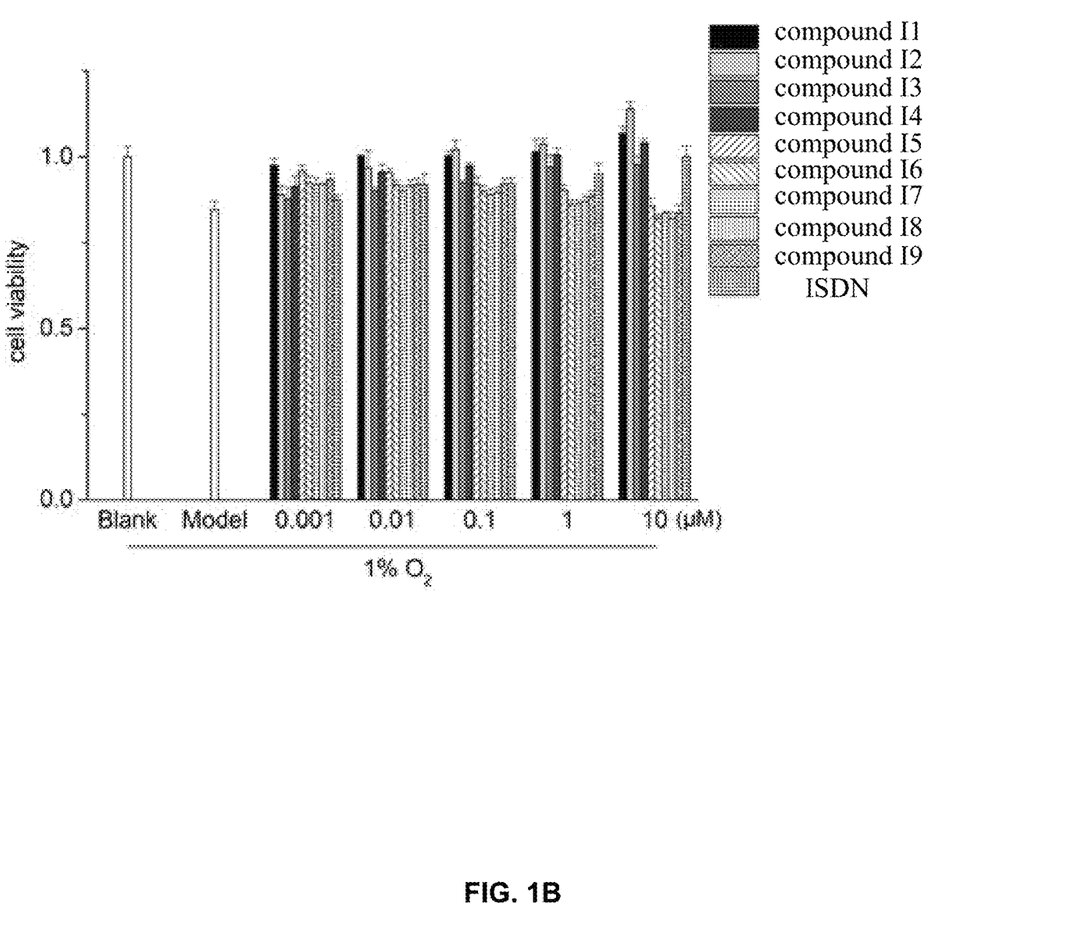
FIG. 1B shows the effect of the NO donor compound on improving the vitality of cardiomyocyte H9c2 under the hypoxic conditions.

Under the normoxic condition (as shown in FIG. 1A), for compounds I1-I9, with the increase of concentration, compound I4 has a slight improvement on the cell viability at the concentration of 1 μM, and other compounds does not have any improvement on the cell viability. On the contrary, the compounds I1-I9 have some effect on the cell viability at a high concentration of 10 μM, showing less toxicity. Under the hypoxic condition (as shown in FIG. 1B), compounds I1-I4 can significantly restore the viability of hypoxic cells in the concentration range of 0.001~10 μM, and the viability of hypoxic cells increases with the increase of compound concentration, while compounds I5-I9 have no significant improvement on the viability of hypoxic cells. The control drug isosorbide dinitrate does not improve the cell viability under the normoxic condition, and has a certain improvement on the cell viability at high concentration under the hypoxic condition, but not as good as compounds I1-I4. Combining the data in Tables 1 and 2, the hypoxia-activated NO donor compounds I1-I4 can effectively release NO under the hypoxic condition and improve the viability of cells in a certain concentration range, and the activity of the compounds I1-I4 is better than that of the existing drug isosorbide dinitrate. This beneficial effect has also been verified in animal level experiments.

Example 14: Detection of NO Release Level of Compound I1 in the Heart of Mouse Hypoxia Model Using NO Detection Kit (a) Drugs, Reagents, and Experimental Animals NO detection kit (Biyuntian Biotechnology Co., Ltd., Shanghai), heart tissue homogenate of hypoxia modeling and drug-given mouse, and blank control group mouse, and 6-8-week-old male Kunming mouse.

(b) Experimental Principle

NO has chemical activity and is rapidly converted into $NO_3^-$ and $NO_2^-$ in the body, and $NO_2^-$ is further converted into $NO_3^-$. $NO^{3-}$ is reduced to $NO_2^-$ using Griess reagent, $NO_2^-$ has characteristic absorption at 540 nm, the absorbance is detected at 540 nm by a microplate reader, and the NO concentration is calculated using a standard curve.

Figure 2:
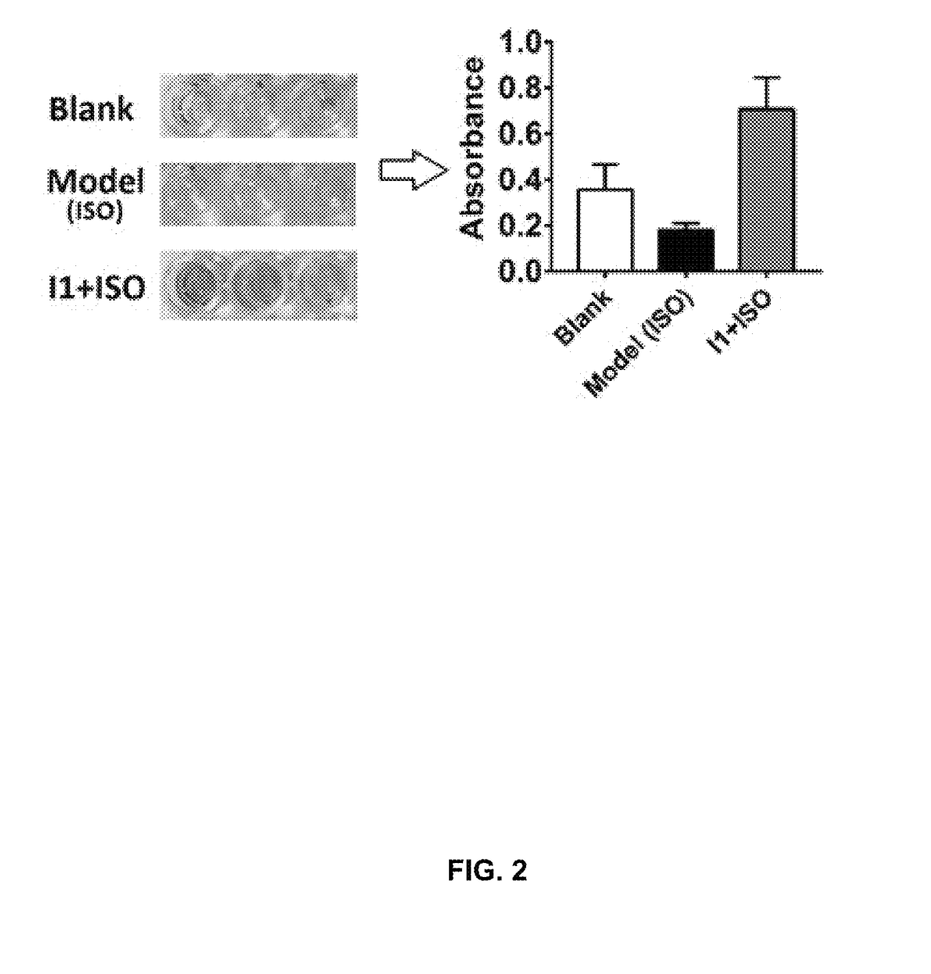
FIG. 2 shows the NO release level of the NO donor compound I1 in the heart of mouse hypoxia model.

(c) Experimental Operation (1) Hypoxia model (85 mg/kg isoproterenol), the drug-given group was intraperitoneally injected with 20 mg/kg compound I1 before hypoxia modeling;

(2) Cardiac tissue homogenate protein was obtained by centrifugation at 12,000 rpm for 15 min;

(3) The working solution in the NO detection kit was prepared, the working solution was added to each group of proteins, after incubation, and each group of proteins was detected with an microplate reader to analyze the NO content in each group, as shown in FIG. 2.

As shown in FIG. 2, after hypoxia modeling and drug-given on mouse, the NO level in the heart of the compound I1 group is significantly higher than that of the other two groups.

Example 15: Study on Regulatory Effect of Compound I1 on the Expression Level of Myocardial Injury Marker Proteins in Myocardial Hypoxia Mouse Using Western Blot (a) Drugs, Reagents, and Experimental Animals Western Blot gel preparation kit (Biyuntian Biotechnology Co., Ltd., Shanghai), BCA detection kit for protein quantification (Biyuntian Biotechnology Co., Ltd., Shanghai), ionization buffer, wet transfer solution, primary antibody (anti-TSC2-P, Abgent, 1:1000, A-AP3825a; anti-mTORC1, Abcam, 1:1000, ab120224; anti-GAPDH, Bioworld Technology, 1:500, AP0063), secondary antibody (Goat Anti-Rabbit IgG (H+L) HRP, 1:3000, Bioworld Technology, BS13278), 6-8-week-old male Kunming mouse.

(b) Experimental Principle

The changes of protein expression levels are analyzed based on Western Blot bands.

(c) Experimental Operation (1) Mouse heart tissue protein was extracted and centrifuged at 12,000 rpm for 15 min to collect the protein, the protein was quantified using a BCA kit, and added to boiling water in loading buffer and cook for 5 min for later use;

(2) SDS-PAGE gel was prepared and the sample was loaded to separate protein bands;

(3) After transferring the protein bands to the PVDF membrane, the membrane was blocked with milk to incubate primary and secondary antibodies in sequence. The protein bands were visualized using a chemiluminescence developer to analyze the changes of protein expression in each group, as shown in FIG. 3.

Figure 3:
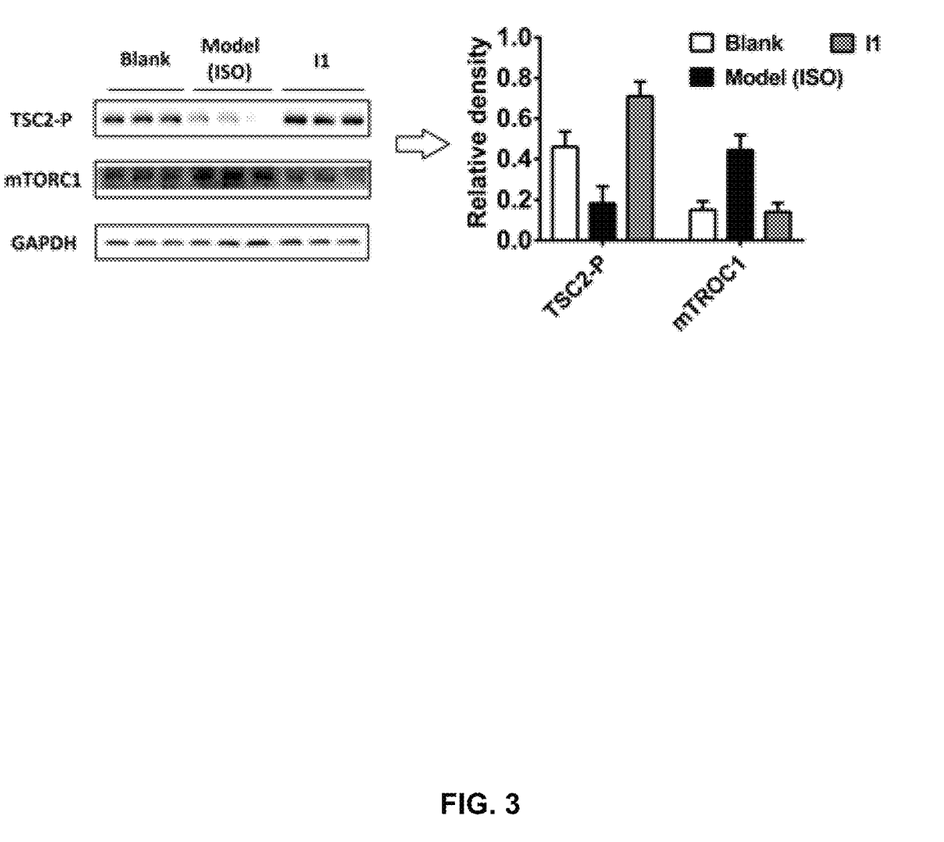
FIG. 3 shows expression level of mTORC1 and TSC2-P proteins in the mouse heart.

As shown in FIG. 3, protein samples were extracted from the hearts of blank group mouse, hypoxia model mouse, and drug-given and hypoxia modeling mouse for Western blot experiments. Compared with the blank group, the down-regulation of TSC2-P expression in the hypoxia model group causes a significant upregulation of mTORC1 protein expression, indicating that the hypoxia model group had obvious myocardial damage. The expression of mTORC1 in the hearts of mouse pretreated with 20 mg/kg compound I1 is restored to near a level of the normal group, indicating that the compound I1 has excellent anti-myocardial hypoxic damage effect.

What is claimed is:

1. A NO donor compound, wherein a structure of the NO donor compound is represented by a formula I:

wherein:
when R1 is nitro group, R2 is selected from the group consisting of hydrogen, halogen, and $C_1$-$C_4$ alkyl, R3 is selected from the group consisting of hydrogen, halogen, and $C_1$-$C_4$ alkyl; or
when R2 is selected from the group consisting of nitro group, R1 is hydrogen, halogen, and $C_1$-$C_4$ alkyl, and R3 is selected from the group consisting of hydrogen, halogen, and $C_1$-$C_4$ alkyl.

2. The NO donor compound of claim 1, wherein in the formula I, R1 is nitro group, R2 is selected from the group consisting of hydrogen, halogen, and methyl, and R3 is hydrogen.

3. The NO donor compound of claim 1, wherein the NO donor compound is selected from the group consisting of following compounds I1-I4:

-continued

I4

4. A method for preparing the NO donor compound of claim 1, comprising: obtaining the NO donor compound of formula I by acylation reaction between compound 1 and compound 2 as follows:

5. A pharmaceutical composition, comprising the NO donor compound of claim 1 and a pharmaceutically acceptable carrier.

* * * * *